United States Patent

Kaali

[11] Patent Number: 5,334,150
[45] Date of Patent: Aug. 2, 1994

[54] VISUALLY DIRECTED TROCAR FOR LAPAROSCOPIC SURGICAL PROCEDURES AND METHOD OF USING SAME

[76] Inventor: Steven G. Kaali, 88 Ashford Ave., Dobbs Ferry, N.Y. 10522

[21] Appl. No.: 978,092

[22] Filed: Nov. 17, 1992

[51] Int. Cl.$^5$ ............................................. A61M 5/176
[52] U.S. Cl. ............................. 604/164; 604/158; 604/264; 606/185
[58] Field of Search ............. 128/3, 4; 604/164, 158, 604/264; 606/185, 15

[56] References Cited

U.S. PATENT DOCUMENTS

| | | | |
|---|---|---|---|
| 1,147,408 | 7/1915 | Kells | 604/164 |
| 3,556,085 | 1/1971 | Takahashi | 128/6 |
| 3,613,684 | 10/1971 | Sheridan | 604/264 |
| 3,653,388 | 4/1972 | Tenckhoff | 604/164 |
| 4,112,932 | 9/1978 | Chiulli | 604/264 X |
| 4,498,902 | 2/1985 | Ash et al. | 604/164 |
| 4,895,431 | 1/1990 | Tsujiuchi et al. | 128/4 X |
| 4,901,142 | 2/1990 | Ikuno et al. | 128/4 X |
| 4,972,827 | 11/1990 | Kishi et al. | 128/3 |
| 5,057,082 | 10/1991 | Burchette, Jr. | 604/164 |
| 5,066,288 | 11/1991 | Deniega et al. | 604/164 X |
| 5,098,388 | 3/1992 | Kulkashi et al. | 604/164 X |
| 5,104,388 | 4/1992 | Quackenbush | 604/164 X |
| 5,163,941 | 11/1992 | Garth et al. | 606/108 |

FOREIGN PATENT DOCUMENTS

0484725A1  5/1992  Fed. Rep. of Germany .

Primary Examiner—Richard J. Apley
Assistant Examiner—Beverly A. Meindl
Attorney, Agent, or Firm—Rodman and Rodman

[57] ABSTRACT

A new and improved laparoscopic trocar and sleeve assembly in which the trocar is provided with a transparent tip and accommodates a light telescope for supplying a video console so that while the trocar is being surgically inserted through the abdominal wall and into the abdominal cavity, visualization on the video console will be possible to avoid injury to blood vessels in the abdominal cavity wall or injury to any of the internal organs located in the abdominal cavity. Once clear visualization is established, conventional laparoscopic procedures can be carried out safely.

29 Claims, 2 Drawing Sheets

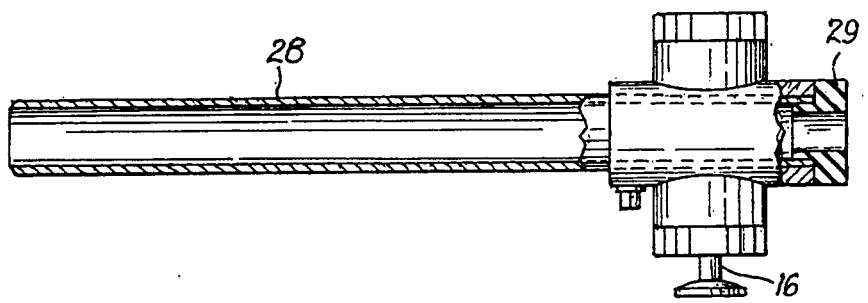
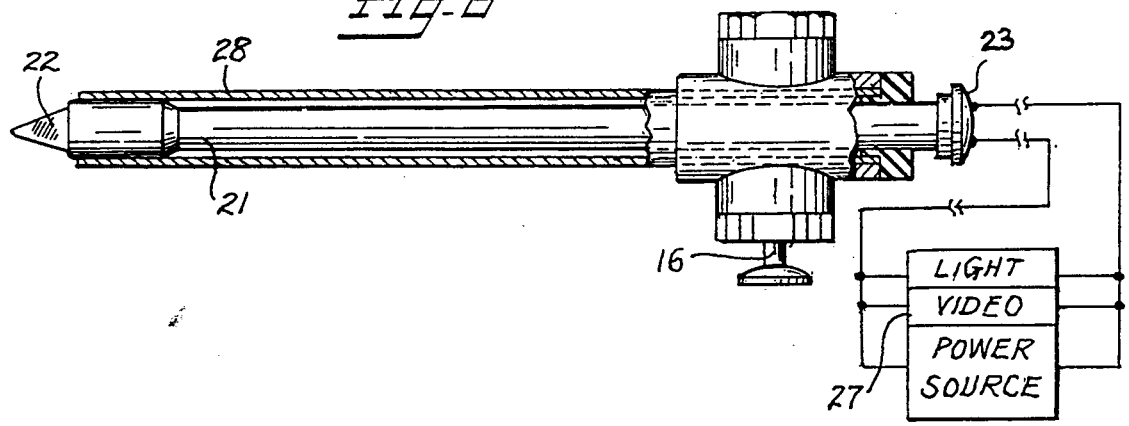
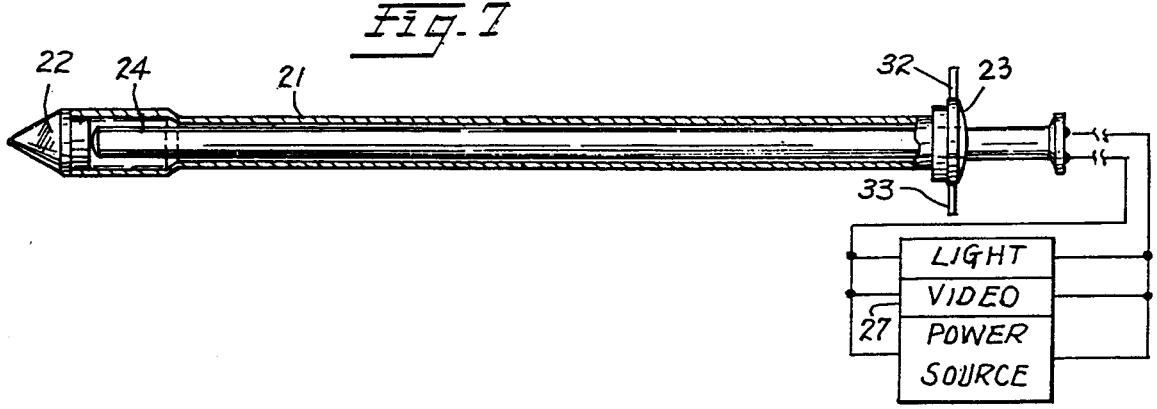

VISUALLY DIRECTED TROCAR FOR LAPAROSCOPIC SURGICAL PROCEDURES AND METHOD OF USING SAME

TECHNICAL FIELD

This invention relates to the field of operative and diagnostic laparoscopic surgical procedures and in particular to a new and improved visually directed trocar laparoscopic instrument and method of use for conducting such procedures.

BACKGROUND OF INVENTION

Operative and diagnostic laparoscopy is the most commonly performed surgical procedure in the United States today. Therefore, any complication associated with this procedure poses a major public health concern.

Conventional known laparoscopic procedures usually are carried out as follows:

1. An instrument known as the Veress needle is blindly inserted through the navel into the abdominal cavity of a patient.
2. Carbon dioxide is delivered blindly through the Veress needle into the abdomen.
3. A laparoscopy trocar assembly comprised by a trocar and trocar sleeve is blindly inserted through the navel into and through the abdominal wall of the abdominal cavity.
4. The trocar is withdrawn from the trocar sleeve and a light telescope with light source placed in the sleeve thus making visualization of the interior of the cavity possible.
5. Once clear visualization is established a variety of surgical procedures can be carried out safely through the central opening in the trocar sleeve with remotely operable surgical instruments in a conventional known manner.

There are several reports in the medical literature that the first two steps of a laparoscopic procedure as outlined above can be omitted, and the laparoscopic trocar assembly directly be inserted blindly into the abdominal cavity. Results of these papers indicate that complications can still be expected since the entry through the abdominal cavity wall into the abdominal cavity remains blind.

SUMMARY OF INVENTION

It is therefore a primary purpose of this invention to make available a new and improved, visually directed, laparoscopic instrument which allows the laparoscopic surgeon to enter the abdominal or other cavity of a patient under direct vision. This visually directed laparoscopic procedure will eliminate most if not all major and minor complications associated with the blind invasive surgical technique presently employed in laparoscopic procedures as described above. In practicing the invention a new and improved laparoscopic instrument is provided with an elongated, hollow trocar having a tipped end suitable for insertion through layers of human skin and flesh forming the walls of a cavity with the tipped end being fabricated from light transparent material. The tipped end of light transparent material preferably is shaped to form a light transmission and imaging element for projecting light outwardly into an abdominal or other cavity of a patient, and for receiving back and directing light images onto a suitable light image receptor of a conventional miniaturized light telescope designed for surgical purposes. The hollow trocar has a central passageway formed therein of sufficient diameter to accommodate the elements of a miniaturized light telescope together with essential power supply conductors for energizing the light source and light receptors such as a bundle of fiber optic light coupling elements for deriving and providing back light images usable for laparoscopic diagnostic procedures even while the trocar is being surgically inserted through the navel and is penetrating through the layers of skin and abdominal wall of a patient and on into the abdominal cavity.

In preferred embodiments of the invention, the laparoscopic instrument includes a hollow tubular trocar sleeve that surrounds and encloses the trocar for a substantial portion of its length to form a combined trocar and sleeve assembly. The trocar is slidable lengthwise relative to the trocar sleeve whereby the trocar can be removed after visually controlled physical placement of the trocar and sleeve assembly into the abdominal wall of a patient's abdominal cavity at a desired location and to a desired depth. The trocar then can be replaced with a somewhat large fiber optic light telescope and video imaging system, and other remotely manipulatable surgical instrument inserted through the central opening of the trocar sleeve in a conventional known manner.

The invention makes available a new and improved laparoscopic procedure comprising mounting a miniaturized light telescope with light source together with suitable miniaturized power supply conductors, and fiber optic coupling and light receptor elements in the hollow trocar prior to starting the laparoscopic procedure. The light telescope then is energized from an electric power source and the output of the light receptors supplied to a video display. Following this setup, the tipped and lighted end of the trocar is placed at a point, such as the navel, on a patient's abdomen to be penetrated while observing such placement on the video display. The lighted trocar then is surgically inserted by being pressed slowly and carefully into and through the walls of the patient's abdomen while observing the progress of the trocar assembly as it travels into and through the wall of the abdominal or other cavity. During this process, the operator, by properly controlling orientation and progress of the trocar tip, can assure that the trocar does not penetrate into the abdominal cavity at a place or for a distance where it might injure any blood vessels within the abdominal cavity walls or internal organs within the abdominal cavity.

BRIEF DESCRIPTION OF DRAWINGS

These and other objects, features and many of the attendant advantages of this invention will be appreciated more readily as the same becomes better understood from a reading of the following detailed description, when considered in connection with the accompanying drawings, wherein like parts in each of the several figures are identified by the same reference characters, and wherein:

FIG. 5 is a longitudinal view of a hollow trocar sleeve suitable for use with the new and improved trocar shown in FIG. 4;

FIG. 6 is a longitudinal sectional view of a new and improved combined hollow trocar and sleeve assembly employing the elements of FIGS. 4 and 5, and constructed in accordance with the invention; and FIG. 7 is longitudinal sectional view of an alternative form of a new and improved hollow trocar having extra exterior handles constructed according to the invention.

BEST MODE OF PRACTICING THE INVENTION

Figure 1:
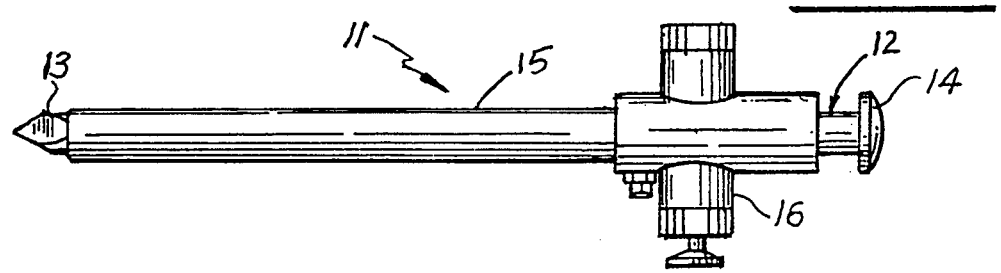
FIG. 1 is a side elevational view of a known, combined trocar and sleeve assembly with trumpet valve and stopcock components constructed according to the prior art.
Figure 2:
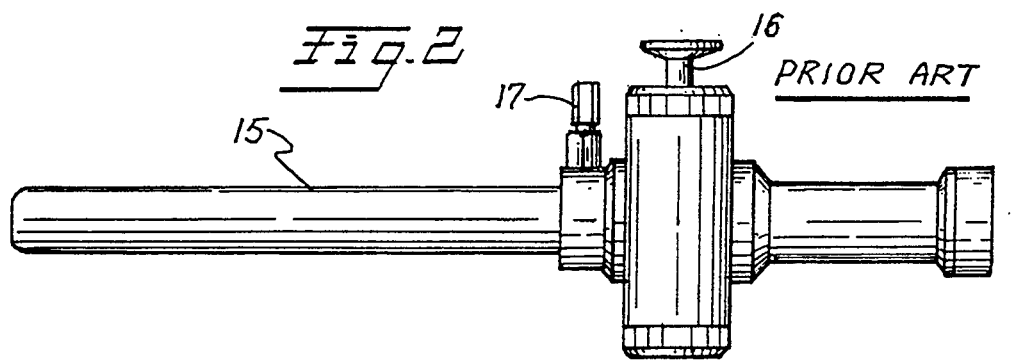
FIG. 2 is a side elevational view of a known trocar sleeve having a different trumpet valve construction from the assembly shown in FIG. 1 and built according to the prior art.
Figure 3:
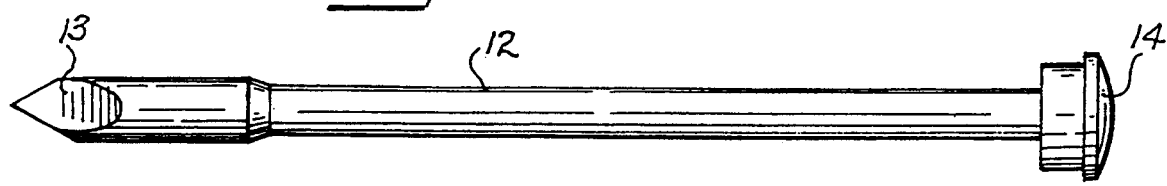
FIG. 3 is a side elevational view of a known trocar design suitable for use with the sleeve shown in FIG. 2 and built according to the prior art.

As noted earlier in the brief description of the drawings, FIGS. 1, 2 and 3 of the drawings illustrate a prior art, known trocar and sleeve assembly now being used by the medical profession in performing laparoscopic procedures such a laparoscopic cholecystectomies. Other similar laparoscopic procedures can be performed using the instrument. In these drawings, FIG. 1 is an elevational side view of a known combined trocar and trocar sleeve assembly 11 comprised by an elongated, solid, stainless steel, trocar 12 best seen in FIG. 3 and a hollow, tubular trocar sleeve 15 shown in FIG. 2. Trocar 12 includes a pointed tipped end 13, which may be either pyramidal or conical in configuration, and is sufficiently sharp to be able to penetrate and be physically pressed through the navel, layers of skin and abdominal walls of a patient in order to provide access to the interior of the abdominal cavity. Trocar 12 is a solid rod of appropriate diameter, for example of from 6 to 9 millimeters in diameter, and terminates in a push cap 14 that facilitates surgical insertion of the stiff elongated rod 12 into and through the navel of a patient by pushing on cap 14.

The trocar 12 is physically supported within the trocar sleeve 15 shown in FIG. 2 of the drawings. Trocar sleeve 15 is a cylindrical hollow tube fabricated from biologically compatible material, such as stainless steel. Sleeve 15 has a central opening into which the trocar 12 fits in a relatively tight manner, but is sufficiently loose to allow trocar 12 to be slid lengthwise relative to the sleeve 15 and withdrawn. Trocar sleeve 15 in most applications also includes at least one trumpet valve 16 as shown in both FIGS. 1 and 2 as well as one or more insufflation stopcocks shown at 17 in FIG. 2. These elements all are of known construction and operation and need not be described in detail with respect to the present invention. In use the assembled trocar and sleeve appear as shown at 11 in FIG. 1 of the drawings.

As described earlier in the specification, conventional laparoscopic procedure is carried out by first blindly inserting a Veress (not shown) through the navel into the abdominal cavity of the patient. Carbon dioxide gas then is delivered blindly through the Veress needle into the abdomen in an effort to draw the skin of the abdomen on which the navel is disposed away from any organs resting internally within the abdominal cavity and to improve visualization within the cavity. It is at this point that the laparoscopic trocar and sleeve assembly 11 is blindly inserted through the navel into the abdominal cavity.

After insertion of the trocar and sleeve assembly 11, the trocar 12 is withdrawn from the trocar sleeve 15 leaving the sleeve with its appended elements such as the trumpet valve 16 and insufflation stopcock 17 extending into the abdominal cavity. A light telescope with a miniaturized light source of conventional commercially available construction is inserted through the central opening of the trocar sleeve 15 to establish visualization of the intra abdominal organs. Once clear visualization is established, a variety of surgical procedures can be carried out safely through the use of remotely operable surgical instruments inserted into the interior of the abdominal cavity through the central passageway in the trocar sleeve 15 in a known manner. Upon completion of the procedures, all instruments including the light telescope are withdrawn along with the trocar sleeve and the opening through which they were inserted is sewn up.

It is believed apparent that the step of introducing the trocar and sleeve assembly into the abdominal cavity using conventional known techniques, is a blind procedure and frequently causes injury to blood vessels in the walls of the abdominal cavity and organs located within the abdominal cavity close to the point of entry.

Figure 4:
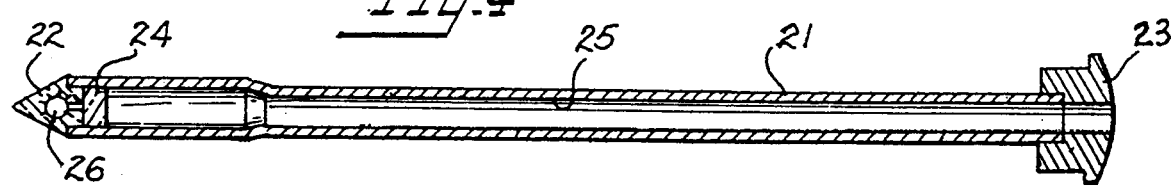
FIG. 4 is a longitudinal sectional view of a new and improved trocar having a transparent tipped end constructed according to the invention.

In order to avoid possible injury to the blood vessels and/or internal organs, the present invention was devised and is illustrated in FIGS. 4, 5 and 6 of the drawings together with FIG. 7 which shows an alternative construction of the trocar according to the invention.

FIG. 4 is a longitudinal sectional view taken along the longitudinal axis of an elongated, cylindrically-shaped trocar having a hollow tubular body 21 fabricated from an inflexible material (such as stainless steel) that is compatible with human flesh. Trocar 21 has a tipped end 22 that is sufficiently sharp that it can be surgically inserted through layers of skin and human flesh by physically pressing on a push cap 23 secured to the opposite end of the trocar. Tipped end 22 is fabricated from light transparent material such as glass or a space-age plastic and is shaped to form a light transmission and imaging element for projecting light outwardly into an abdominal or other cavity of a patient and for directing light images received back onto a suitable light image receptor 24. Tipped end 22 also has a substantially solid piercing point, as shown in FIG. 4 which can be of pyramidal or conical configuration.

Light image receptor 24 is part of a commercially available, miniaturized, medical light telescope for surgical use and is not part of this invention. Receptor 24 may comprise a plurality of light receiving input ends of a bundle of fiber optic light coupling elements (not shown) or alternatively a semiconductor light to electric signal transducer. Trocar 21 has a central opening 25 which is of sufficient diameter to accommodate passage of the elements of the miniaturized light telescope such as a light source 26 comprised by a bundle of fiber optic elements, a semiconductor laser or a light bulb together with essential power supply conductors and/or fiber optic light coupling elements (not shown). These elements serve to energize light source 26 and light receptors 24 (or traducers if required) together with fiber optical or electric signal coupling elements for deriving and supplying video signals to a video camera 27, comprising a part of the light telescope system. The video camera 27 excites a suitable video monitor (not shown) for producing video images usable for diagnostic and surgical purposes even while the trocar is being surgically inserted into and is penetrating the layers of skin on the navel prior to proceeding into the abdominal cavity.

Trocar 21 shown in FIG. 4 is designed for use with a trocar sleeve 28 shown in FIG. 5. Trocar sleeve 28 comprises an elongated hollow tubular body of stainless steel or other similar material having an open end through which the tipped transparent end 22 of trocar 16 projects and a rubber sealing cap 29 on the opposite end. Preferably a trumpet valve 21 and insufflation stopcock, such as 17 shown in FIG. 2, are included on the hollow trocar sleeve 28. If desired, the trocar sleeve 15 shown in FIG. 2 and trocar sleeve 28 in FIG. 5 can be made to be interchangeable.

Trocar sleeve 28 is designed to physically surround and enclose trocar 21 for a substantial portion of its length to form a combined trocar and sleeve assembly shown in FIG. 6 of the drawings. The trocar 21 is slidable lengthwise relative to trocar sleeve 28 so that the trocar can be removed after visual surgical insertion of the trocar 21 and sleeve 28 assembly into the abdominal cavity of a patient at a desired location and to a desired depth. After removal of trocar 21, it is replaced with a suitable known fiber optic light source and video imaging system (not shown) and supplemented with other remotely manipulatable surgical instruments (not shown) which can be inserted through the central opening of the trocar sleeve 28 in a conventional, known manner.

FIG. 7 illustrates an alternative design of the trocar 21 wherein suitable handles shown at 32 and 33 are provided on opposite sides of the elongated tubular body of the trocar 21 at the end opposite transparent tip end 22. In all other respects, the trocar of FIG. 7 is similar to that described with relation to FIG. 4. Surgical insertion of the trocar 21 of FIG. 7 and trocar sleeve 28 in assembled relation as depicted by FIG. 6, through the navel of a patient can be better accomplished and more easily guided using the handles 32 and 33 while visually observing the progress of the trocar through the layers of skin and abdominal walls of a patient. By observing the pre-imminent entry of the trocar assembly into the abdominal cavity under conditions where the position of blood vessels in the walls of the abdominal cavity and internal organs located within the abdominal cavity can be observed, prior to thrusting the trocar all the way into the cavity, injury to the blood vessels and internal organs can be avoided.

In conducting a laparoscopic procedure employing the novel, hollow, laparoscopic trocar 21 with a tipped end 22 fabricated from light transparent material shaped to form a light transmission and receiving element, the procedure is commenced by activating the miniaturized light telescope including the light source and suitable miniaturized light receptors, power supply conductors and fiber optic couplings provided in the assembled hollow trocar and sleeve, while using the trocar of either FIG. 4 or FIG. 7, prior to starting the procedure. After the light source is activated, any output from the light receptors 24 is supplied to a video display console (not shown) via video receiver 27. The tipped and lighted end of the trocar 21 then is placed at the point on the patient's abdomen (such as the navel) to be penetrated while observing such placement on the video display. The trocar and sleeve assembly then is pushed slowly into and through the layers of skin and support flesh of the patient's navel while observing the progress of the trocar assembly on the video display while it travels into and through the navel. During this process, the positioning of the trocar can be adjusted by the laparoscopic surgeon, if necessary, by manipulation of the push cap 23 and/or side handles 32 and 33, to assure that the trocar does not penetrate into the abdominal cavity at a place or for a distance where it might penetrate and injure blood vessels in the walls of the cavity or internal organs within the abdominal cavity.

In the above recited procedure, the combined assembly of trocar 21 and trocar sleeve 28 are inserted together with the light source and video display components of the miniaturized light telescope contained therein. After completing the visually directed insertion of the combined trocar and sleeve assembly as described above, the trocar 21 together with its light source and video display components is removed from sleeve 28 which remains implanted in the abdominal cavity. The trocar 21 then is replaced in implanted sleeve 28 with the fiber optic light source and video imaging system of the miniaturized light telescope along with any other assorted remotely manipulatable surgical instruments, as needed, which are inserted through the central opening in the trocar sleeve in a conventional known manner.

PRACTICAL APPLICABILITY

This invention provides to the medical profession a new laparoscopic instrument which allows the laparoscopic surgeon to enter the abdominal cavity of a patient under conditions where he can directly, visually follow the progress of the pointed tip of the instrument as it passes through the layers of skin and supporting walls of the abdominal cavity. Hence, prior to entering the abdominal cavity to any great depth, the surgeon can observe whether there are any blood vessels in the supporting walls or internal organs which would be punctured or otherwise damaged if the trocar is allowed to penetrate too deeply at a selected point. The new procedure and instrument will eliminate many major and minor complications associated with the prior known blind invasive laparoscopic surgical techniques employed to implant the laparoscopic trocar and sleeve assembly into the abdominal cavity.

Having described two embodiments of a new and improved laparoscopic instrument and procedure according to the invention, it is believed obvious that other modifications and variations of the invention will be suggested to those skilled in the art in the light of the above teachings. It is therefor to be understood that changes may be made in the particular embodiments of the invention described which are within the full intended scope of the invention as defined by the appended claims.

What is claimed is:

1. A new and improved laparoscopic instrument comprising an elongated, hollow tubular member of inflexible material compatible with human flesh, and having a tipped and suitable for insertion through human flesh to form a hollow trocar, said tipped end formed essentially of light transparent material with a substantially solid piercing point, said tipped end affixed to said hollow tubular member and shaped to form a light transmission and imaging element for projecting light outwardly into an abdominal or other cavity of a patient and for imaging light images received back onto a suitable light image receptor.

2. A laparoscopic instrument according to claim 1 wherein the hollow trocar has a central passageway formed therein of sufficient diameter to accommodate passage of a miniaturized light source together with essential power supply conductors for energizing the light source and any light receptors for further accommodating fiber optic light coupling elements for deriving and providing back usable light images for supply to a video camera that excites a suitable video monitor for producing images usable for diagnostic purposes and surgical procedures even while the trocar is being surgically inserted into and is penetrating the layers of skin and wall of a patient's abdomen.

3. A laparoscopic instrument according to claim 1 wherein the hollow trocar is provided with a blunt end and readily grasped handles extending outwardly from the blunt end of the trocar whereby the trocar more readily can be physically grasped and pressed through the navel of a patient and maneuvered to avoid injury to the blood vessels in the walls of the abdomen and internal organs in the abdominal cavity.

4. A laparoscopic instrument according to claim 2 wherein the hollow trocar is provided with a blunt end and readily grasped handles extending outwardly from the blunt end of the trocar whereby the trocar more readily can be physically grasped and pressed through the navel of a patient and maneuvered to avoid injury to blood vessels in the walls of the abdomen and any internal organs in the abdominal cavity.

5. A laparoscopic instrument according to claim 1 further including a hollow trocar tubular sleeve of relatively inflexible material compatible with human flesh physically surrounding and enclosing said trocar for a substantial portion of its length to form a combined trocar and sleeve assembly, the trocar being slidable lengthwise relative to the sleeve and removable whereby the trocar can be removed after visual surgical insertion of the trocar and sleeve assembly into the flesh of a patient at a desired location and to a desired depth, and the trocar replaced with a fiber optic light source and video imaging system of a light telescope and other remotely manipulatable surgical instruments inserted through the central opening of the trocar sleeve in a conventional known manner.

6. A laparoscopic instrument according to claim 2 further including a hollow trocar tubular sleeve of relatively inflexible material compatible with human flesh physically surrounding and enclosing said trocar for a substantial portion of its length to form a combined trocar and sleeve assembly, the trocar being slidable lengthwise relative to the sleeve and removable whereby the trocar can be removed after visual surgical insertion of the trocar and sleeve assembly into the flesh of a patient at a desired location and to a desired depth, and the trocar replaced with a fiber optic light source and video imaging system of a light telescope and other remotely manipulatable surgical instruments inserted through the central opening of the trocar sleeve in a conventional known manner.

7. A laparoscopic instrument according to claim 5 wherein the tubular trocar sleeve is provided with at least one trumpet valve subassembly, an insufflation stopcock and one or more seals and sealing caps for maintaining the trocar sleeve gastight and safely usable for laparoscopic procedures.

8. A laparoscopic instrument according to claim 6 wherein the tubular trocar sleeve is provided with at least one trumpet valve subassembly, an insufflation stopcock and one or more seals and sealing caps for maintaining the trocar sleeve gastight and safely usable for laparoscopic procedures.

9. A laparoscopic instrument according to claim 1 wherein said substantially solid piercing point is of pyramidal configuration.

10. A laparoscopic instrument according to claim 1 wherein said substantially solid piercing point is of conical configuration.

11. A new and improved laparoscopic procedure comprising the steps of:
 a) employing a novel hollow laparoscopic trocar with a tipped end formed essentially of transparent material and a substantially solid piercing point extending from said tipped end, said tipped end being designed for surgical insertion into human flesh where said tipped end is shaped to form a light transmission and receiving element;
 b) mounting a miniaturized light source, suitable miniaturized light receptors, power supply conductors, and fiber optic coupling and light receptor devices of a conventional light telescope in the hollow trocar;
 c) coupling the light source to an electric power source for energizing the light source;
 d) coupling the output of the light receptors to a video display;
 e) placing said tipped end at the point on a patient's abdomen to be penetrated while observing such placement on the video display;
 f) surgically inserting said trocar into and slowly through the layers of skin and wall of the patient's abdomen while observing the progress of said trocar on the video display as said trocar travels into and through the navel; and
 g) maneuvering said trocar to assure that said trocar does not penetrate blood vessels in the abdominal cavity wall or injure internal organs within the abdominal cavity.

12. A new and improved laparoscopic procedure according to claim 11 wherein the hollow trocar is part of an assembly further comprised by a hollow trocar sleeve physically surrounding and enclosing said trocar for a substantial portion of its length, the trocar being slidable lengthwise relative to the sleeve; and wherein the trocar together with its light source and video display components of a light telescope are removed after placement of the trocar and sleeve assembly into the abdominal cavity at a desired and safe place and depth in a directly observed careful manner; and the trocar is replaced with a fiber optic light source and video imaging system of another light telescope along with as well as other assorted remotely manipulatable surgical instruments, as needed, which are inserted through the central opening in the trocar sleeve in a conventional known manner.

13. A new and improved laparoscopic procedure according to claim 10 wherein the tubular trocar sleeve is provided with at least one trumpet valve subassembly, an insufflation stopcock and one or more seals and sealing caps for maintaining the trocar sleeve gastight; and wherein prior to insertion of the trocar into the abdominal cavity, an insufflation needle is inserted into the abdominal cavity and the abdominal cavity is inflated by delivering a biocompatible gas through the needle to increase the free space in the abdomen and facilitate the insertion of the trocar assembly and to provide space for surgical procedures to be carried out within the abdominal cavity.

14. A surgical penetration device comprising:
a) an inflexible elongated member having a first end,
b) light transmission and imaging means provided at the first end of said elongated member to project light and receive light images,
c) said light transmission and imaging means including means for piercing human flesh to permit surgical insertion of said light transmission and imaging means through human flesh into a body cavity,
d) said light transmission and imaging means being affixed to said first end of said inflexible elongated member and formed essentially of transparent material,
e) said piercing means having a substantially solid piercing point, and
f) said elongated member having means for containing a lighting means and a light image receiving means to cooperate with said light transmission and imaging means.

15. The surgical penetration device as claimed in claim 14 wherein said elongated member is hollow.

16. The surgical penetration device as claimed in claim 14 wherein said elongated member is a cylinder.

17. The surgical penetration device as claimed in claim 14 wherein said light transmission and imaging means has a tapered section and a nontapered section, a predetermined amount of said nontapered section being recessed in the first end of said elongated member.

18. The surgical penetration device as claimed in claim 17 wherein the nontapered section of said light transmission and imaging means is substantially circular in cross section.

19. The surgical penetration device as claimed in claim 14 wherein said light transmission and imaging means is integrally joined to said elongated member at said first end of said elongated member.

20. The surgical penetration device as claimed in claim 14 wherein said light transmission and imaging means is formed of glass.

21. The surgical penetration device as claimed in claim 14 wherein said light transmission and imaging means is formed of plastic.

22. The surgical penetration device as claimed in claim 14 wherein said elongated member has a second end opposite said first end, and a handle member being provided proximate said second end to facilitate manipulation of said elongated member.

23. A surgical penetration device according to claim 14 wherein said substantially solid piercing point is of pyramidal configuration.

24. A surgical penetration device according to claim 14 wherein said substantially solid piercing point is of conical configuration.

25. A method of visualizing insertion of a surgical device through flesh into a body cavity comprising the steps of:
a) providing a novel hollow trocar with a tubular body and a tipped end formed essentially of transparent material, said tipped end having a substantially solid piercing point and forming a light transmission and imaging member such that said light transmission and imaging member pierces human flesh for surgical insertion through human flesh,
b) joining said light transmission and imaging member to one end of said tubular body formed of a biocompatible material,
c) locating a conventional lighting means and light image receiving means in said hollow trocar proximate said light transmission and imaging member to enable light from the lighting means to project outwardly away from said light transmission and imaging member and to permit the light image receiving means to receive light images that pass from outside said light transmission and imaging member through said light transmission and imaging member while said light transmission and imaging member is being inserted through the flesh into a body cavity, whereby said light transmission and imaging member provides a receivable image of the flesh and body cavity being entered.

26. The method of claim 21 including slidably locating said hollow trocar with said light transmission and imaging member in a sleeve and fixing the position of said hollow trocar relative to the sleeve such that substantially only the light transmission and imaging member projects from one end of the sleeve to permit insertion of the sleeve with the light transmission and imaging member through the flesh into a body cavity.

27. The method of claim 25 including monitoring the light images received by the light image receiving means on a video screen while the light transmission and imaging member is being inserted through the flesh into a body cavity to obtain continuous video aided visual imaging of the internal location of the light transmission and imaging member during such insertion.

28. The method of claim 25 including the step of forming said substantially solid piercing point with a pyramidal configuration.

29. The method of claim 25 including the step of forming said substantially solid piercing point with a conical configuration.

* * * * *

UNITED STATES PATENT AND TRADEMARK OFFICE
CERTIFICATE OF CORRECTION

PATENT NO. : 5,334,150
DATED : August 2, 1994
INVENTOR(S) : Steven G. Kaali

It is certified that error appears in the above-identified patent and that said Letters Patent is hereby corrected as shown below:

In column 4, line 63, change "traducers" to --transducers--.

In column 5, line 10, change "21" to --16--.

In column 6, line 58, change "and" to --end--.

In column 8, line 57, change "10" to --12--.

In column 10, line 31, change "21" to --25--.

Signed and Sealed this

Twenty-seventh Day of May, 1997

Attest:

BRUCE LEHMAN

Attesting Officer

Commissioner of Patents and Trademarks